(12) United States Patent
Tulleken et al.

(10) Patent No.: US 11,259,809 B2
(45) Date of Patent: Mar. 1, 2022

(54) BLOOD VESSEL CONNECTORS AND METHODS FOR BLOOD VESSEL CONNECTION

(71) Applicant: AMT MEDICAL B.V., Uithoorn (NL)

(72) Inventors: Cornelis Antonius Franciscus Tulleken, Uithoorn (NL); Jappe Onno Tunnis Noest, Uithoorn (NL); Hendricus Jacobus Mansvelt Beck, Uithoorn (NL); Alexander Cornelis Elisabeth Van Thoor, Uithoorn (NL); David Stecher, Uithoorn (NL); Glenn Bronkers, Uithoorn (NL)

(73) Assignee: AMT MEDICAL B.V., Uithoorn (NL)

( * ) Notice: Subject to any disclaimer, the term of this patent is extended or adjusted under 35 U.S.C. 154(b) by 481 days.

(21) Appl. No.: 15/947,573

(22) Filed: Apr. 6, 2018

(65) Prior Publication Data
US 2018/0221025 A1   Aug. 9, 2018

Related U.S. Application Data

(63) Continuation of application No. 14/369,649, filed as application No. PCT/NL2012/050747 on Oct. 26, 2012, now abandoned.

(60) Provisional application No. 61/586,073, filed on Jan. 12, 2012.

(51) Int. Cl.
*A61B 17/11* (2006.01)
*A61B 17/08* (2006.01)

(52) U.S. Cl.
CPC ............. *A61B 17/11* (2013.01); *A61B 17/083* (2013.01); *A61B 2017/1103* (2013.01); *A61B 2017/1107* (2013.01); *A61B 2017/1121* (2013.01); *A61B 2017/1132* (2013.01); *A61B 2017/1135* (2013.01); *A61B 2017/1139* (2013.01)

(58) Field of Classification Search
CPC .............. A61B 17/11; A61B 17/083; A61B 2017/1103; A61B 2017/1107; A61B 2017/1121; A61B 2017/1132; A61B 2017/1135; A61B 2017/1139
See application file for complete search history.

(56) References Cited

U.S. PATENT DOCUMENTS

| 4,917,087 A | 4/1990 | Walsh et al. |
| 6,187,020 B1 * | 2/2001 | Zegdi ................. A61B 17/1152 606/152 |

(Continued)

FOREIGN PATENT DOCUMENTS

| WO | 98-29040 | 7/1998 |
| WO | 2004-086985 | 10/2004 |
| WO | 2011-062495 | 5/2011 |

*Primary Examiner* — Jing Rui Ou
(74) *Attorney, Agent, or Firm* — Nixon & Vanderhye

(57) ABSTRACT

Various embodiments of the present disclosure include an apparatus comprising a clip which includes a first side including a first ring configured to pass over an end of a first vessel, the first ring configured to engage the first side with the first vessel, and a second side coupled to the first side, the second side including a second ring configured to pass over an end of a second vessel, the second ring being configured to engage the second side with the second vessel. The first and second sides, when in a closed position, are configured to maintain the first and second vessels in substantially end-to-end contact.

1 Claim, 14 Drawing Sheets

(56) References Cited

U.S. PATENT DOCUMENTS

| | | | | |
|---|---|---|---|---|
| 7,022,131 B1* | 4/2006 | Derowe | ......... | A61B 17/320758 |
| | | | | 623/1.11 |
| 7,828,814 B2* | 11/2010 | Brenneman | .......... | C09K 8/5753 |
| | | | | 606/151 |
| 8,361,092 B1* | 1/2013 | Asfora | .................. | A61B 17/08 |
| | | | | 606/153 |
| 2005/0131432 A1 | 6/2005 | Gold et al. | | |
| 2005/0234483 A1* | 10/2005 | Yencho | ................. | A61B 17/11 |
| | | | | 606/153 |
| 2005/0251183 A1* | 11/2005 | Buckman | ............... | A61B 17/08 |
| | | | | 606/157 |
| 2010/0036398 A1* | 2/2010 | Aboud | ................ | A61B 17/083 |
| | | | | 606/153 |
| 2013/0053862 A1* | 2/2013 | Tulleken | ................ | A61B 17/11 |
| | | | | 606/108 |

* cited by examiner

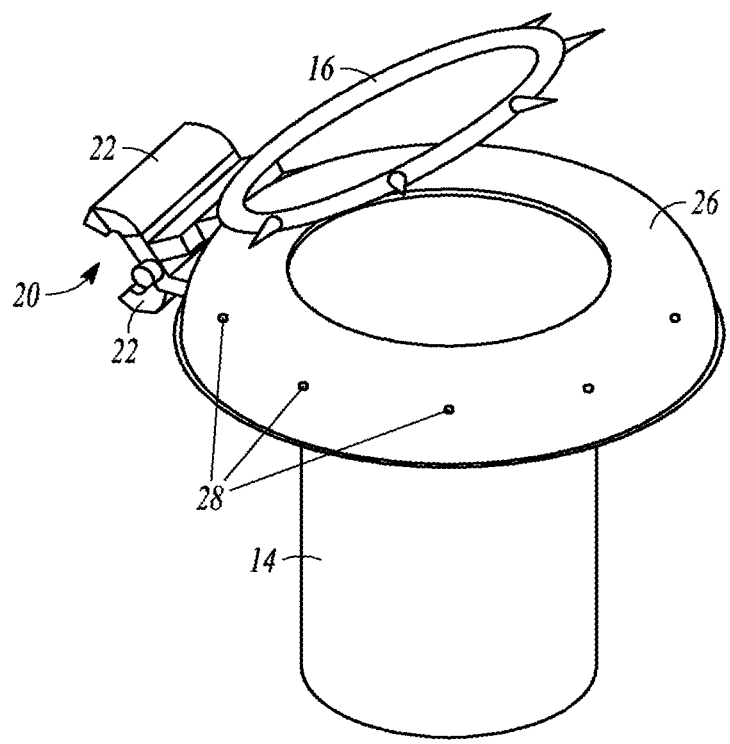
FIG. 1C
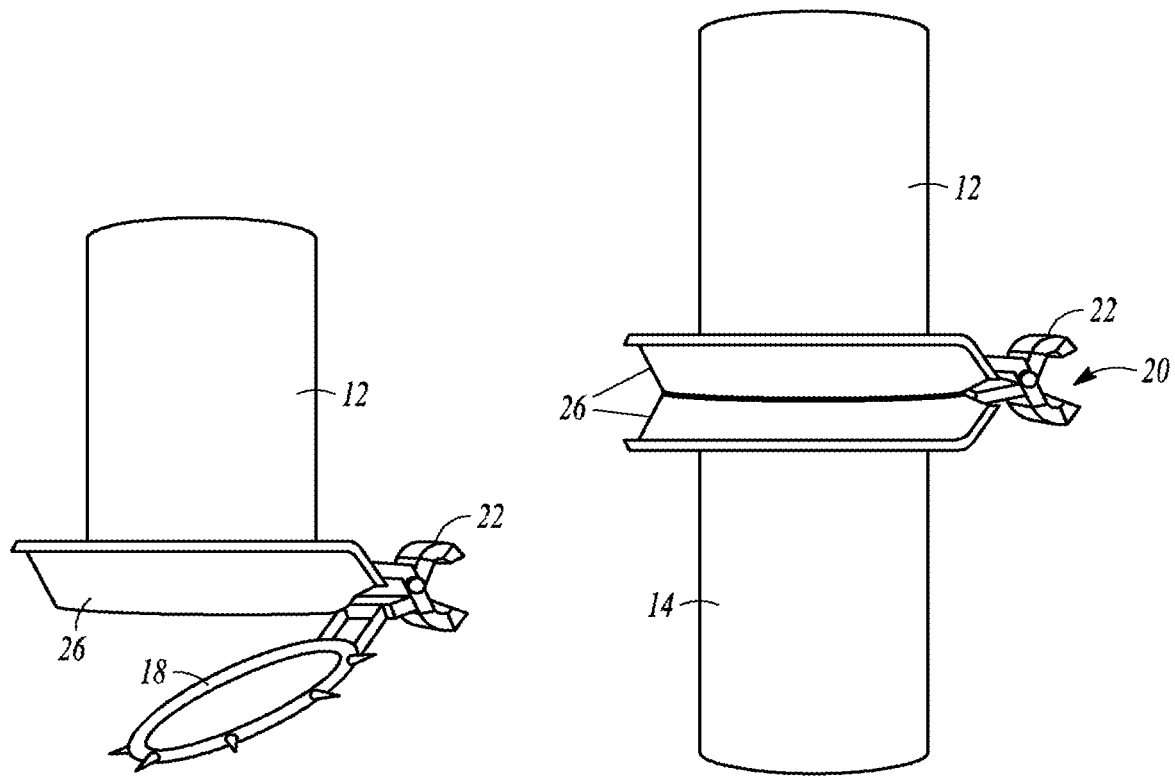
FIG. 1D     FIG. 1E

| NUMERAL | DIMENSION (mm) |
|---|---|
| A | 5.7 |
| B | 3.5 |
| C | 1.6 |
| D | 2.96 |
| E | 45° |
| F | 15° |
| G | R 0.1 |
| H | 0.5 |
| I | 13.2° |
| J | R 0.6 |
| K | 0.81 |
| L | 12.6° |

BLOOD VESSEL CONNECTORS AND METHODS FOR BLOOD VESSEL CONNECTION

CLAIM OF PRIORITY

This patent application claims the benefit of priority to Tulleken et al, U.S. Provisional Patent Application Ser. No. 61/586,073, entitled "Blood Vessel Connectors and Methods for Blood Vessel Connection", filed on Jan. 12, 2012, which is hereby incorporated by reference herein in its entirety.

FIELD

The present subject matter relates to the field of surgery, including methods for fusing or otherwise connecting body tissues, such as blood vessels. In particular, the invention is useful during vascular surgery for creating anastomoses and for vascular reconstruction.

BACKGROUND

Fusion of body tissues for repairing tissues, including when closing surgical openings, as well as for creating new connections of tissue, such as an anastomosis for vascular bypass, has been an important concern of surgeons since surgical procedures were first used.

In vascular surgery, anastomoses need to be made to join vessels with other vessels or open volumes through which blood can flow. Such tissue connections should be made blood-tight, and be able to withstand the pressures and forces acting on them in vivo.

The creation of a fluid or blood-tight (hemostatic) and mechanically stable connection such as for an anastomosis takes considerable time, skill, and care and is prone to complications. Even slight misalignment, asymmetric tension, introduction of foreign material, or wrong tissue types may trigger bodily responses, such as thrombogenesis, coagulation, or scar formation, which may have a detrimental effect on the patency (i.e., the ability to let fluids pass) of a connection, or cause immediate or delayed leakage of vessels or vessel damage, later followed by dehiscence, pseudo aneurysm, or anastomotic aneurysm formation.

In most cases, tissue joints such as the ones required in an anastomosis are created when the surgeon sutures or staples tissues, such as vessel wall tissues, together. Tissue soldering, tissue welding, and the use of adhesives have also been discussed, but the first two methods are not widely used, while adhesives are generally only used in combination with sutures, clips, or mechanical closures.

A common concern associated with the use of adhesives, especially when connecting blood vessels, is that the adhesive may enter the bloodstream leading to blockage and other complications. In addition, using adhesives alone to join body tissues can result in mechanically unsafe connections or connections with insufficient patency. The tissues to be joined can be under a different tension during surgery than in vivo, or can be subject to varying tensions, which can result in the weakening or breaking of an adhesive bond between the tissues or a change in the form of a connection. Although methods of using adhesives to connect a graft to an unoccluded recipient vessel were described decades ago (see, U.S. Pat. No. 3,805,793 to Wright, which was issued in 1974), adhesives are generally not used by themselves in surgical procedures for the reasons stated above, despite the apparent advantages that adhesives seem to offer, in particular, ease of application.

In many clinical applications, it is advantageous to perform anastomosis without occluding the recipient vessel. This becomes particularly important when the recipient vessel involved performs a vital function. In generally sensitive or critical organs such as the brain and the heart, occluding a recipient vessel even temporarily is often disadvantageous. A technique commonly referred to as the ELANA (Excimer Laser Assisted Nonocclusive Anastomosis) technique, is used in clinical practice to create an anastomosis without occluding the recipient vessel (see also, U.S. Pat. No. 5,964,750 (Tulleken et al.)). This technique is, for example, used by neurosurgeons in bypass surgery.

There exists a need in the art for an improved method for attaching body vessels to each other. More specifically, there exists a need for attaching body vessels in so-called "end-to-end", "end-to-side", or "side-to-side" fashions. There is also a need for an improved anastomotic surgery aid for forming connections between body vessels.

SUMMARY

In general, the present invention addresses the above-described needs by providing improved methods for attaching body vessels to each other as well as for improved anastomotic surgery aids.

In one aspect, an apparatus comprises a clip which includes a first side including a first ring configured to pass over an end of a first vessel, the first ring configured to engage the first side with the first vessel; and a second side coupled to the first side, the second side including a second ring configured to pass over an end of a second vessel, the second ring configured to engage the second side with the second vessel, the first and second sides, when in a closed position, being configured to maintain the first and second vessels in substantially end-to-end contact.

In another aspect, an apparatus comprises a clip including a first side including a first attachment portion configured to engage a side wall of a first vessel; and a second side coupled to the first side, the second side including a second attachment portion configured to engage a side wall or an end of a second vessel, the first and second sides, when in a closed position, being configured to maintain the first and second vessels in side-to-side contact, or in side-to-end contact, respectively.

EXAMPLES

To better illustrate the apparatus and methods disclosed herein, a non-limiting list of examples is provided here:

1. An apparatus comprising a clip including a first side including a first ring configured to pass over an end of a first vessel, the first ring configured to engage the first side with the first vessel; and a second side coupled to the first side, the second side including a second ring configured to pass over an end of a second vessel, the second ring configured to engage the second side with the second vessel, the first and second sides, when in a closed position, being configured to maintain the first and second vessels in substantially end-to-end contact.

2. The apparatus of example 1, wherein the second side of the clip is hinged to the first side of the clip.

3. The apparatus of example 1 or example 2, wherein the first and second sides are biased to a closed position.

4. The apparatus of any one of examples 1-3, wherein the first or second ring is configured to engage the respective first or second side of the clip to a folded-over portion of the respective first or second vessel end.

5. The apparatus of any one of examples 1-4, wherein a first or second side of the clip includes respective first or second attachment features configured to attach the first or second side of the clip with the first or second vessel.

6. The apparatus of example 5, wherein the first or second attachment features include points configured to puncture a wall of the respective first or second vessel, thereby to attach the first or second side of the clip with the respective first or second vessel.

7. The apparatus of any one of the examples 1-6,
wherein the first side of the clip and the second side of the clip are hinged to each other to be movable between the closed position and an open position,
wherein in the closed position the first ring and second ring are arranged mutually parallel, wherein in the open position the first ring and second ring are arranged at an angle with respect to each other.

8. The apparatus of example 7, wherein the clip comprises a biasing mechanism biasing the first and second side of the clip to the closed position.

9. A method for facilitating connection of first and second vessels, the method comprising obtaining a clip including a first side including a first ring configured to pass over an end of the first vessel, the first ring configured to engage the first side with the first vessel, and a second side coupled to the first side, the second side including a second ring configured to pass over an end of the second vessel, the second ring configured to attach the second side with the second vessel; passing the first ring over the end of the first vessel; passing the second ring over the end of the second vessel; and closing the sides of the clip to bring the first and second vessels in substantially end-to-end contact.

10. The method of example 9, further comprising folding a portion of the end of the first or second vessel over the first or second ring; and attaching the first or second ring to the folded-over portion of the first or second end, respectively.

11. The method of example 10, wherein the first or second side of the clip includes respective first or second attachment features, the first or second attachment features including points configured to puncture a wall of the first or second vessel.

12. The method of example 11, wherein the wall is a wall of the first or second folded-over portion, and wherein the method further comprises inserting the points into the wall to attach the first or second ring to the folded-over portion of the first or second vessel end, respectively.

13. The method of any one of examples 9-12, wherein the first and second sides of the clip are biased to a closed position, and wherein the method further comprises closing the sides of the clip to maintain the first and second vessels in substantially end-to-end contact.

14. An apparatus comprising a clip including a first side including a first attachment portion configured to engage a side wall of a first vessel; and a second side coupled to the first side, the second side including a second attachment portion configured to engage a side wall or an end of a second vessel, the first and second sides, when in a closed position, being configured to maintain the first and second vessels in side-to-side contact, or in side-to-end contact, respectively.

15. The apparatus of example 14,
wherein the first side of the clip and the second side of the clip are movable with respect to each other between the closed position and an open position,
wherein in the closed position the first attachment portion and second attachment portion are arranged mutually parallel,
wherein in the open position the first attachment portion and second attachment portion are arranged at an angle with respect to each other.

16. The apparatus of any one of examples 14-15, wherein the first and second sides are biased to the closed position.

17. The apparatus of any of examples 14-15, wherein the clip comprises a biasing mechanism biasing the first and second side of the clip to the closed position.

18. The apparatus of any one of examples 14-16, wherein the first or second attachment portion includes at least one fork or point configured to puncture the side wall or end of the respective first or second vessel, thereby to engage the first or second side of the clip with the side wall or end of the respective first or second vessel.

19. The apparatus of any one of examples 14-16, wherein the first or second attachment portion includes a pair of forks for insertion into the side wall of the first or second vessel.

20. The apparatus of example 19, wherein the pair of forks defines an outline that stretches or supports a portion of the side wall disposed between the inserted forks.

21. The apparatus of any of examples 18-20, wherein the fork is a two-prong fork.

22. The apparatus of any of examples 14-17, wherein the first attachment portion comprises a first fork with two prongs, and wherein the second attachment portion comprises second fork with two prongs.

23. The apparatus of example 22, wherein each fork has a curved section where the prongs are outwardly curved with respect to each other.

24. The apparatus of example 23, wherein, in the closed position, the curved sections of the first and second fork are nested into each other.

25. The apparatus of example 22, wherein each fork has a rectilinear section where the prongs are substantially parallel to each other.

26. The apparatus of example 25, wherein, in the closed position, the rectilinear sections of the forks are nested into each other.

27. The apparatus of any of examples 21-26,
wherein the prongs of the fork have a pointed distal end to puncture a vessel, and
wherein the fork has a first prong section, a second prong section arranged between the first prong section and the distal ends of the prongs, and a third prong section, which is arranged between the second prong section and the distal ends of the prongs and extends up to the distal ends of the prongs,
wherein the distance between the prongs is, in the second section, smaller than in the first section, and
wherein in the third prong section, viewed in the direction of the distal ends, the prongs diverge with respect to each other.

28. The apparatus of example 27, wherein the distance between the distal ends of the prongs corresponds to the maximum distance between the prongs in the first section.

29. The apparatus of any of examples 14-18,
wherein the first attachment portion includes a first loop having a first leg, a second leg and a reverse bend connecting the first and second leg and extending 180°,
wherein the first leg extends from an end of the loop coupled to the second side to the reverse bend, and
wherein the second leg extends from the reverse bend to a free end of the loop which is pointed to puncture a vessel.

30. The apparatus of examples 29,
wherein the second attachment portion includes a second loop having a first leg, a second leg and a reverse bend connecting the first and second leg and extending 180°, wherein the first leg extends from an end of the loop coupled to the second side to the reverse bend, and wherein the second leg extends from the reverse bend to a free end of the loop which is pointed to puncture a vessel.

31. Apparatus of example 30, wherein, in the closed position, the first and second loop are nested into each other.

32. Apparatus of any of examples 29-31, wherein the first or second loop has an U-shaped configuration.

33. The apparatus of any one of examples 14-32, wherein the first attachment portion on the first side of the clip lies at least partially within the second attachment portion on the second side of the clip when the clip is in the closed position.

34. The apparatus of any one of examples 14-33, wherein the first attachment portion on the first side of the clip lies at least partially on top of the second attachment portion on the second side of the clip when the clip is in the closed position.

35. The apparatus of any one of examples 14-34 further comprising a hinge coupling the first side to the second side of the clip.

36. The apparatus of example 35, wherein the hinge is formed integrally with the clip, the hinge including a deformable material that biases the first and second sides to the closed position, or holds the first and second sides in a desired position.

37. The apparatus of any one of examples 14-36, further comprising a retainer member interposable between the first and second sides of the clip, the retainer member being configured to engage with a side of the clip to open or close a connection between the first and second vessels.

38. The apparatus of example 37, wherein the retainer member includes a ring structure that can allow the passage of blood through the center of the ring structure at least when the connection is closed.

39. The apparatus of example 38, wherein, on the one hand, the ring structure and, on the other hand, at least a part of the first attachment portion or the second attachment portion are, in closed position, nested into each other.

40. The apparatus of any of examples 38-39, further comprising a second retainer member, such as a second ring structure, interposable between the first and second sides of the clip, the second retainer member being configured to engage with a side of the clip to open or close a connection between the first and second vessels.

41. A method for facilitating connection of first and second vessels, the method comprising obtaining a clip including a first side including a first attachment portion configured to engage a side wall of a first vessel, and a second side coupled to the first side, the second side including a second attachment portion configured to engage a side wall or an end of a second vessel, the first and second sides, when in a closed position, being configured to maintain the first and second vessels in side-to-side contact, or in side-to-end contact, respectively; engaging the first attachment portion with the side wall of the first vessel; engaging the second attachment portion with the side wall or the end of the second vessel; and closing the sides of the clip to bring the first and second vessels in substantially side-to-side or side-to-end contact.

42. The method of example 41, wherein the first and second sides of the clip are biased to a closed position, and wherein closing the sides of the clip includes maintaining the first and second vessels in substantially side-to-side or side-to-end contact.

43. The method of example 41 or example 42, wherein the first or second attachment portion includes points or at least one fork configured to puncture the side wall or end of the respective first or second vessel, and wherein the method further includes inserting the points or the at least one fork into the side wall or end of the first or second vessel thereby to engage the first or second side of the clip with the respective side wall or end of the first or second vessel.

44. The method of any one of examples 41-43, wherein the first or second attachment portion includes a pair of forks for piercing the side wall of the first or second vessel, the pair of forks defining an outline that can stretch or support a portion of the side wall disposed between the forks when the forks are embedded in the side wall of the first or second vessel; and wherein the method further comprises inserting the pair of forks into the side wall of the respective first or second vessel, and supporting or stretching a portion of the side wall disposed between the inserted forks.

45. The method of any one of examples 42-44, wherein the clip includes a retainer member interposable between the first and second side soft the clip, the retainer member being configured to engage with a side of the clip to open or close a connection between the first and second vessels, the method further comprising opening or closing at least one of the sides of the clip to open or close the connection.

46. The method of any one of examples 42-45, further comprising forming a hole in the side wall of the first or second vessel.

These and other examples and features of the present apparatus and methods will be set forth in part in the following Detailed Description. The Summary and the Examples are intended to provide non-limiting examples of the present subject matter. It is not intended to provide an exclusive or exhaustive explanation. The Detailed Description is included to provide further information about the present subject matter.

BRIEF DESCRIPTION OF THE DRAWINGS

Embodiments are illustrated by way of example and not limitation in the figures of the accompanying drawings. In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 1A-1E show aspects of an anastomosis clip, according to example embodiments.

FIGS. 3A-3C show aspects of an anastomosis clip, according to example embodiments.

DETAILED DESCRIPTION

The following detailed description includes references to the accompanying drawings, which form a part of the detailed description. The drawings show illustrations in accordance with example embodiments. These example embodiments, which are also referred to herein as "examples," are described in enough detail to enable those skilled in the art to practice the present subject matter. The embodiments may be combined, other embodiments may be utilized, or structural changes may be made without departing from the scope of what is claimed. The following detailed description is, therefore, not to be taken in a limiting sense.

The accompanying figures illustrate generally an example anastomosis clip. In some examples, the anastomosis clip can be used to connect two vessels together. In further examples, the anastomosis clip can be used to connect two vessels substantially end to end, as shown for example in FIG. 1E. The anastomosis clip can be used to connect various vessels together. The vessels may be connected in occlusive or non-occlusive manner. In some examples, the anastomosis clip can be used in a bypass procedure.

Figure 1A:
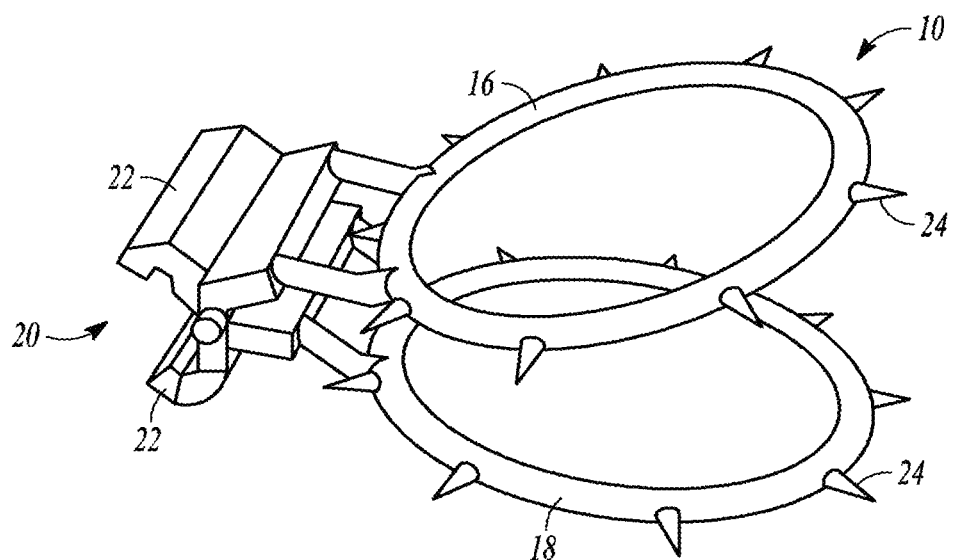
Figure 1B:
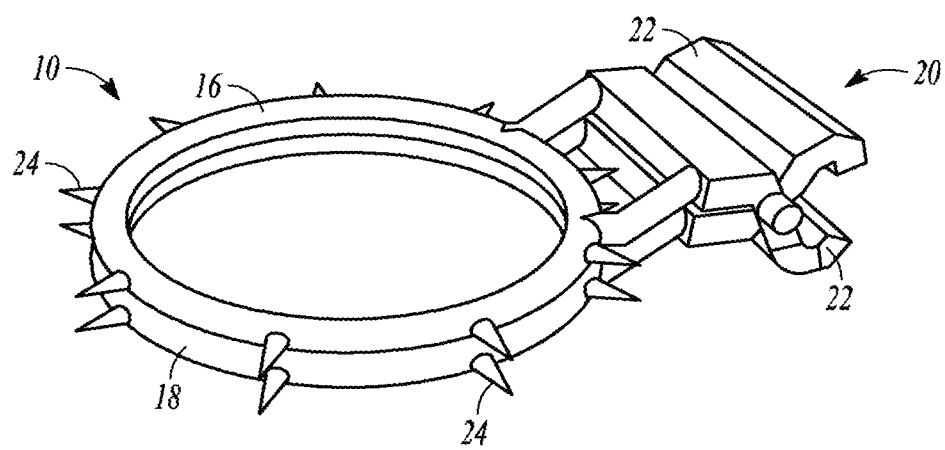

Referring now to FIGS. 1A-1E, an example anastomosis clip 10 includes two rings 16 and 18 coupled together by a hinge shown generally by numeral 20. In some examples, the hinge 20 includes opposed gripping formations 22 that allow the rings 16 and 18 to be manipulated by a suitable applicator (not shown). The applicator may have jaws that can engage with the gripping formations 22 to open and close the clip, for example. In some examples described herein, at least one of the sides of the clip, and in some cases both sides, is biased to a closed position. In some examples, the hinge 20 of the anastomosis clip 10 is biased to a closed position (FIG. 1B). In some examples, the gripping formations 22 can be squeezed together against the bias by an applicator to move the rings 16 and 18 apart (FIG. 1A). In some examples, biasing mechanisms or features can include or use springs or spring-like elements, clamps, "memory" steel or deformable material, and manual clip-closing systems. In some examples, the rings 16 and 18 can be held in a closed or open position by deformation of material included in the hinge 20 or biasing mechanism.

In an example, the rings 16 and 18 have attachment features in the form of points 24 extending radially outwardly from the rings 16 and 18. In some examples, the points 24 are configured to puncture the vessel wall, such as, for instance, the folded-over vessel wall 26 of one or more of the vessels to be joined (FIGS. 1B-1C). In some examples, the points 24 puncture the vessel wall completely such that ends of the points 24 can be seen at exit puncture marks 28 (FIG. 1C). In some examples, the points do not puncture the vessel wall completely. In an example, the rings 16 and 18 have eight points 24, although it is contemplated that the rings include more or less than eight points, or no points (i.e. a smooth ring), or that the rings have different numbers of points from one another. The surface of the rings may be roughened to provide a textured surface. The points or roughened surface can assist in avoiding slippage of the connected vessels or avoid slippage of the vessels relative to the rings. The points can also improve the stability of the connected vessels leading to improved hemastosis. Some points 24 might be configured to extend in different directions or angles relative to a plane or axis of the ring. In some examples, the points 24 include different point configurations of features, for example a pin configuration, or a hook configuration, or one or more teeth, or a hardened surface (for example, diamond), or may include biocompatible or bio-absorbable material.

Figure 2C:
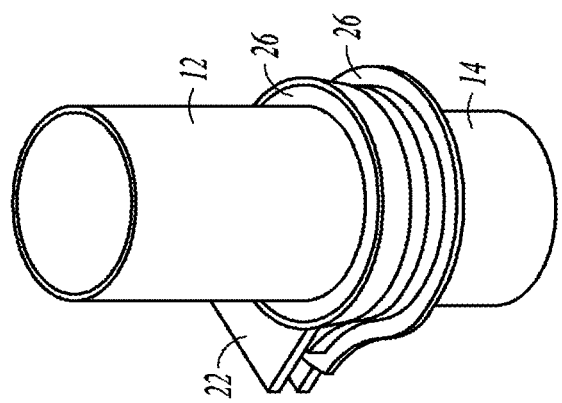
FIGS. 2A-2C show aspects of a method for facilitating connection of first and second vessels, according to example embodiments.
Figure 2B:
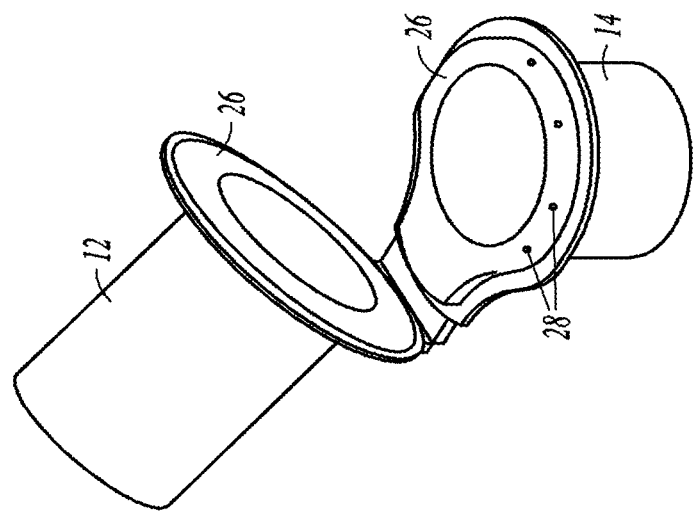
Figure 2A:
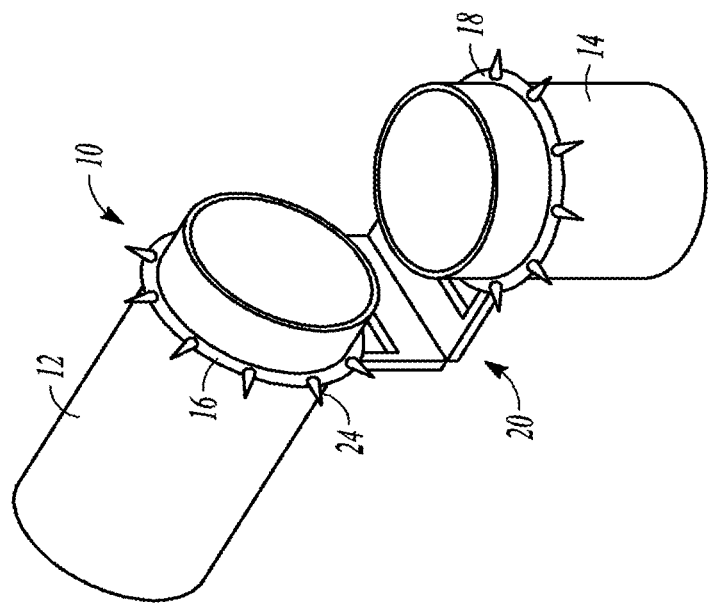

Reference is now made to FIGS. 2A-2C of the accompanying drawings. FIG. 2A shows two vessel ends 12 and 14 in contact with the anastomosis clip 10, with one vessel end placed through each of the rings 16 and 18 of the anastomosis clip 10. FIG. 2B shows the ends of the vessels 12 and 14 being folded over, shown generally at 26, with the points of one of the rings penetrating through the vessel wall at 28 to attach the ring of the anastomosis clip 10 with the vessel wall. This connection can avoid slippage. FIG. 2C shows each vessel wall folded over and attached to the corresponding ring of the anastomosis clip 10, with the anastomosis clip 10 in the closed position to connect the vessels 12 and 14 substantially end-to-end. Since both vessel walls are folded an intima to intima contact is facilitated. This can be important in surgical procedures. In some examples, the anastomosis clip 10 (and the hinge 20 thereof) is sufficient to maintain the vessels 12 and 14 in end-to-end contact without the need of separate fasteners, such as sutures, for instance. However, in other examples, it is contemplated that one or more additional fasteners can be used with the anastomosis clip.

Figure 3C:
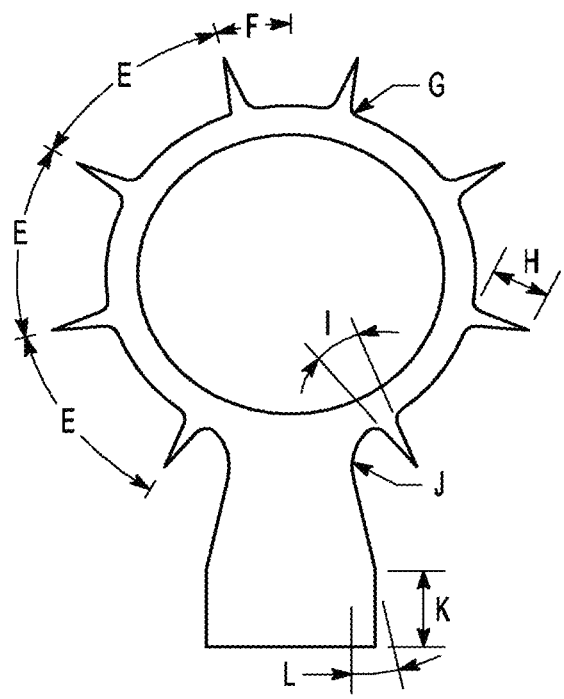
Figure 3C:
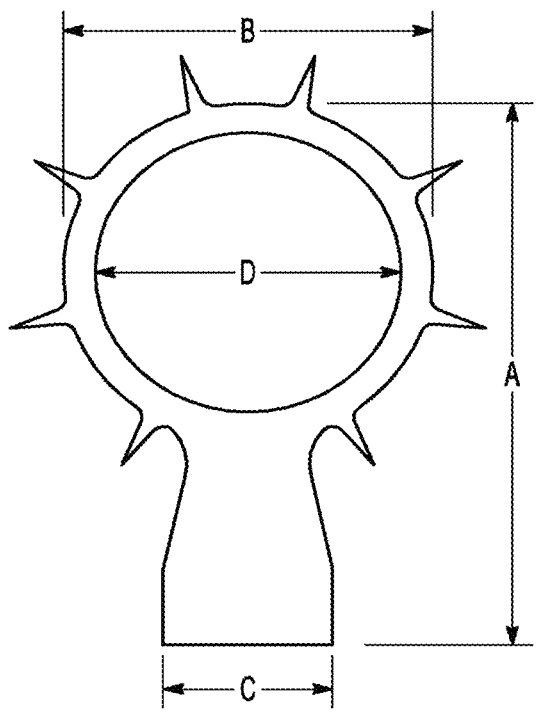
Figure 4A:
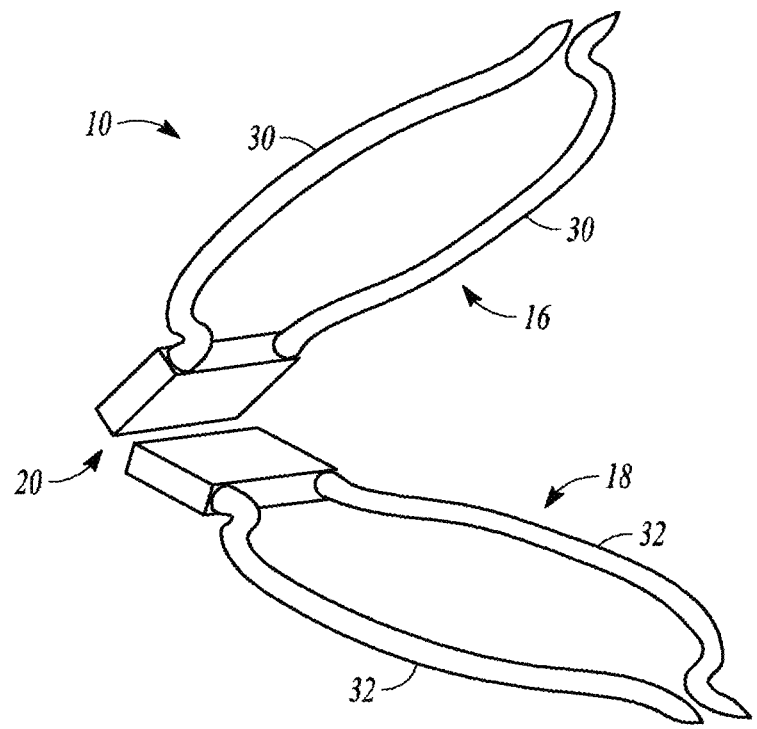
FIG. 4A-4D show aspects of an anastomosis clip, according to example embodiments.
Figure 4B:
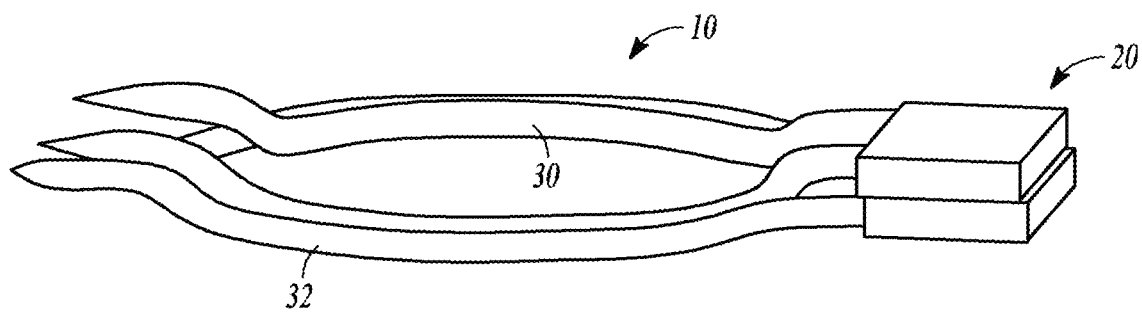
Figure 4C:
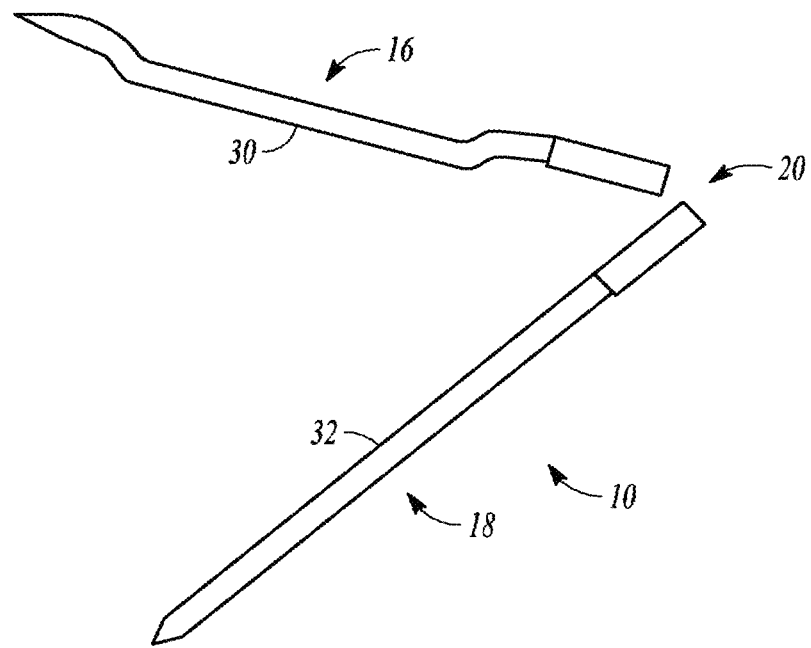
Figure 4D:
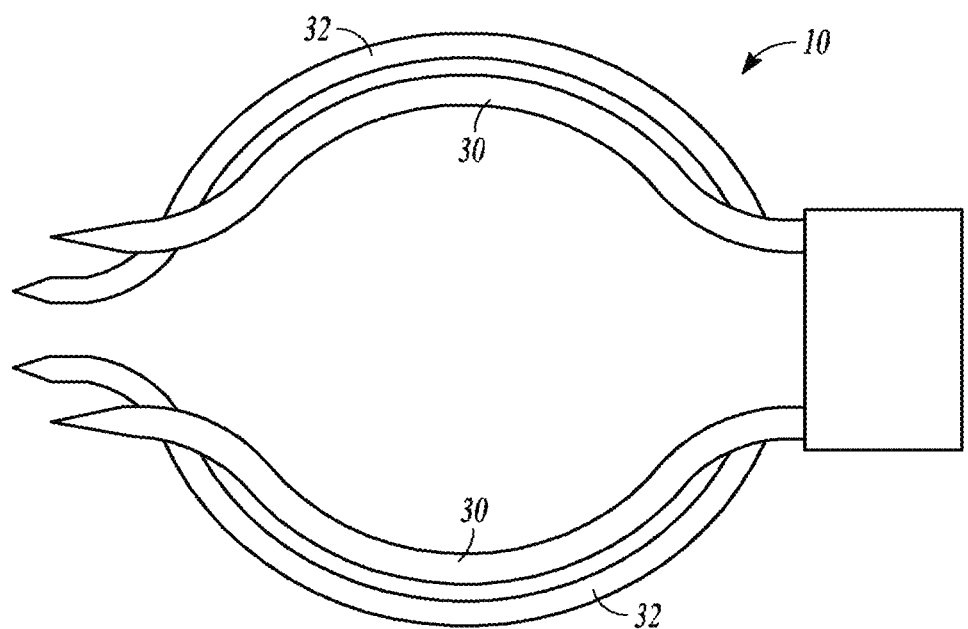

FIGS. 3A-3B show an example of a side of the anastomosis clip 10 of FIGS. 1A-2C. Each side of the anastomosis clip 10 can be identical, in some examples. In other examples, the sides of the anastomosis clip can differ in shape, size, or configuration. A circular shape is shown for both rings in the accompanying drawings, but other shapes for the rings individually or collectively are possible. The overall or greatest size of a clip 10 can range from a couple of millimeters to a couple of centimeters. Although some dimensions are specified in relation to the clip 10 shown in FIGS. 3A-3B, in various examples, the sides of the clip 10 can have different dimensions, for instance, to fit the vessels intended to be attached. In some examples, the anastomosis clip has the dimensions indicated in the table appearing in FIG. 3C. The numerals listed in that table are marked in FIGS. 3A-3B.

FIGS. 4A-4D generally depict an example anastomosis clip 10. The clip can include two sides 16 and 18 coupled together. In an example, the two sides are hinged together shown generally at 20. In some examples, the hinge 20 of the anastomosis clip 10 is biased to a closed position. In some examples, the clip 10 can include gripping formations and can be manipulated with a suitable applicator, for example in similar manner to the clip 10 described above. In some examples, the present clip 10 includes one or more biasing mechanisms or features, for example biasing mechanisms or features of the type described above.

In some examples, at least one of the sides 16 and 18 of the clip includes an attachment portion configured to attach the side to a corresponding vessel. In some examples, the attachment portion includes attachment features such as forks 30 and 32 configured to pierce the vessel wall. While each side is shown with a two-prong (or paired) fork, it is contemplated that the sides of the anastomosis clip 10 include differently configured attachment features. FIGS. 5A-5F show an example procedure for joining two vessels 12 and 14 together. In some examples, an anastomosis clip 10, as shown, can be used to connect the two vessels. In some examples, the two-pronged forks 30 and 32 are pushed through the walls of a donor and recipient vessel and then the clip 10 is closed. In further examples, the anastomosis clip 10 can be used to connect two vessels side to side. The anastomosis clip 10 can be used to connect various vessels together, including, but not limited to vessels in the brain. In some examples, the anastomosis clip can be used in a bypass procedure.

FIGS. 5A-5D show a first side 18 of the anastomosis clip attached to a first vessel 12 (for instance, a donor vessel). The forks 32 of the first side 18 of the clip 10 have been inserted into the wall of the vessel 12 and therefore the side 18 and the forks 32 are not directly visible in these views. On insertion into the wall of the vessel 12, the outwardly curved configuration of the forks 32 serves to stretch the wall of the vessel 12 somewhat. The stretched wall defines a substantially planar or level surface 36 in the vessel wall. The planar or level surface 36 can facilitate the ability to cut an incision or a hole in, or a flap from, the vessel wall using a laser catheter, a puncher or scissors, for example. The region 36 is generally bounded by the contours of the underlying forks 32 and the wall of the vessel is stretched or at least supported in that region.

If desired, a laser catheter (or other device) can be passed through the first vessel 12 to align a tip of the laser catheter with the surface 36 and to cut through the wall of the first vessel lying within that region. Instead of a laser other devices may be used like punchers or scissors to create an incision or hole in, or flap from, the vessel wall. The laser catheter can be of conventional type. Appropriate cuts by the laser form a hole in the vessel wall allowing the passage of blood. In some examples, a hole is not formed in the region 36 until the two vessels 12 and 14 have first been joined together in the following manner.

Figure 5A:
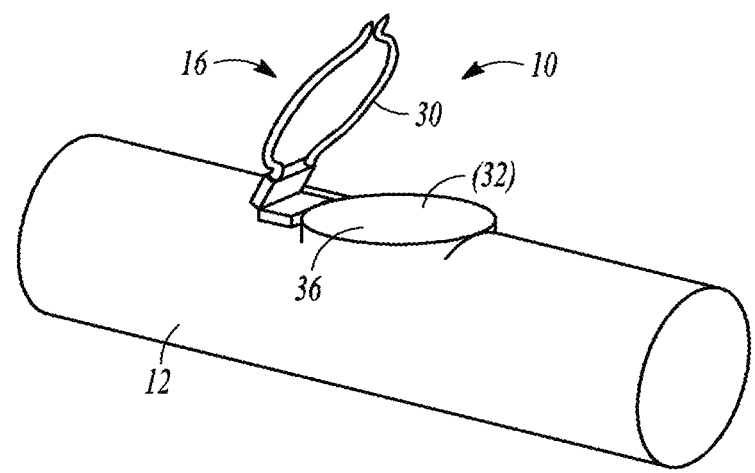
FIGS. 5A-5F show aspects of a method for facilitating connection of first and second vessels, according to example embodiments.
Figure 5B:
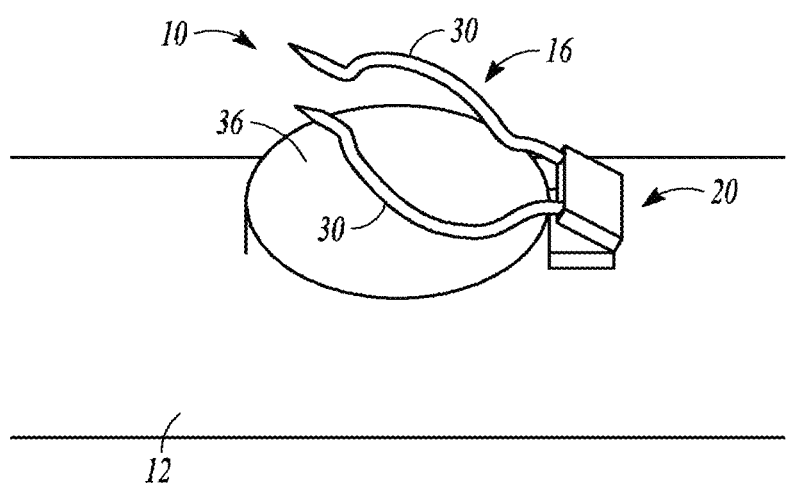
Figure 5C:
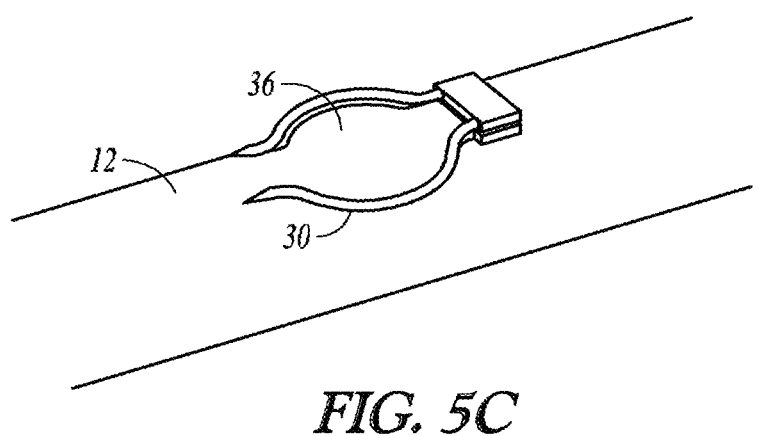
Figure 5D:
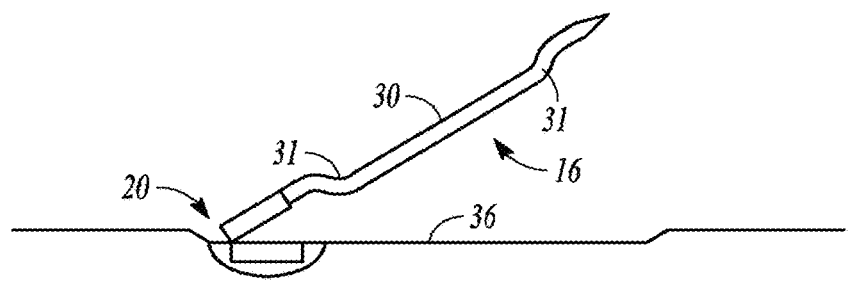

Referring to FIG. 5D, the clip 10 can be placed in an open position such that a second side 16 of the clip which includes the forks 30 is moved away from the wall of the vessel 12. The standing configuration of the forks 30 in an open clip 10 can facilitate entry of the forks into an adjacent vessel wall, but depending on the configuration of the forks 30, or the overall configuration of the clip 10, or the configuration of the sides 16 and 18, the need to open the clip 10 to join one side to another vessel may not always be required. For example, sharp ends of the forks may stand proud of the clip even in a closed position such that the sharp ends are free to be inserted, by sliding action of the clip along the vessel wall, into the vessel wall.

Figure 5E:
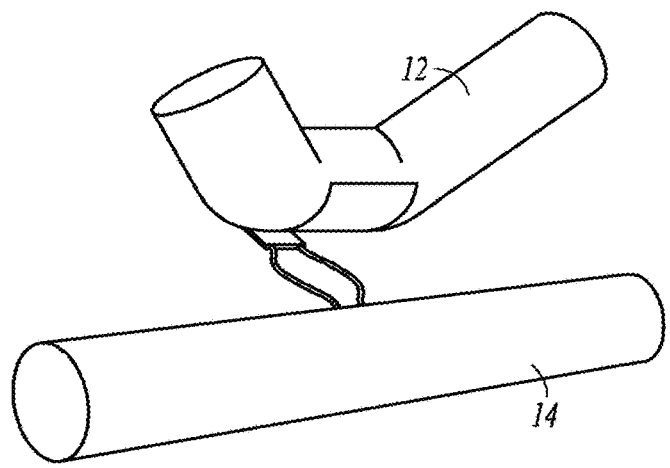
Figure 5F:
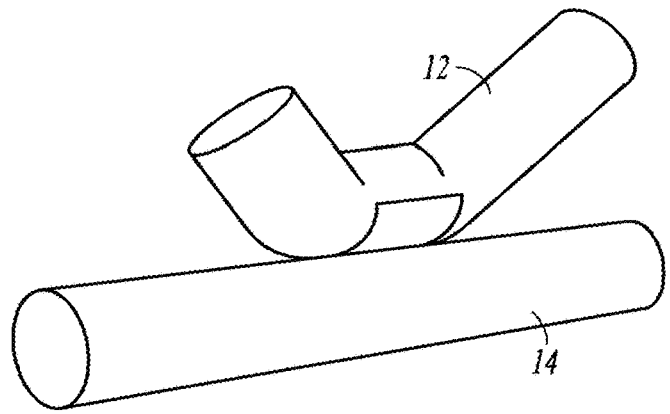

Now referring to FIG. 5E, the second side 16 of the anastomosis clip is then connected with a second vessel 14 (for instance, a recipient vessel) by inserting the forks 30 into the wall of the vessel 14. Once attached, the anastomosis clip 10 can be placed in the closed position to abut the sides of the first and second vessels together, as shown in FIG. 5F.

In the event a hole has already been formed in the first vessel 12 (as described above), the laser catheter (or other device) can then be used to cut a second hole in the side of the second vessel 14 to allow fluid to pass between the first and second vessels 12 and 14 through the now-aligned holes in their sides. If a hole has not previously been formed in the first vessel 12, the laser catheter (or other device) can then be used at this time to cut a "joint" hole in abutting sides of both of the first and second vessels 12 and 14 to allow fluid to pass between the first and second vessels through the "joint" hole. In some examples, the anastomosis clip 10 in the closed position connects the vessels side-to-side, and can disconnect the vessels in the open position. In some examples, the anastomosis clip 10 (and the hinge 20 thereof) is sufficient to maintain the vessels in side-to-side contact without the need of separate fasteners, such as sutures, for instance. However, in other examples, it is contemplated that one or more additional fasteners can be used with the anastomosis clip.

The sides and/or forks of the clip 10 can assume different configurations or be of different sizes relative to one another. For example, and with reference to FIG. 4D, the forks 30 and 32 can have an open ring shape in plan outline, with the diameter of the outer open ring of the forks 32 being larger than the diameter of the inner open ring of the forks 30. This configuration allows an attachment feature on one side of the clip 10 (inserted, for example, into a recipient vessel) to nest within, or at least partially lie inside, an attachment feature on the other side of the clip 10 (inserted, for example, into a donor vessel). In some examples, one side or attachment feature of the clip 10 can lie within the other side or attachment feature of the clip 10 in a "side-by-side" general configuration when the clip 10 is closed. As will be seen at 31 in the side view of FIG. 5D, the contours of the forks 30 are configured or bent out of plane as appropriate to allow such nesting. The nesting configuration can improve fixation of the vessel walls to each other and allow improved hemostasis. In some examples, the rings or attachment features are of similar size and assume an overlapping or "ring-on-ring" general configuration when the clip 10 is closed.

Figure 6A:
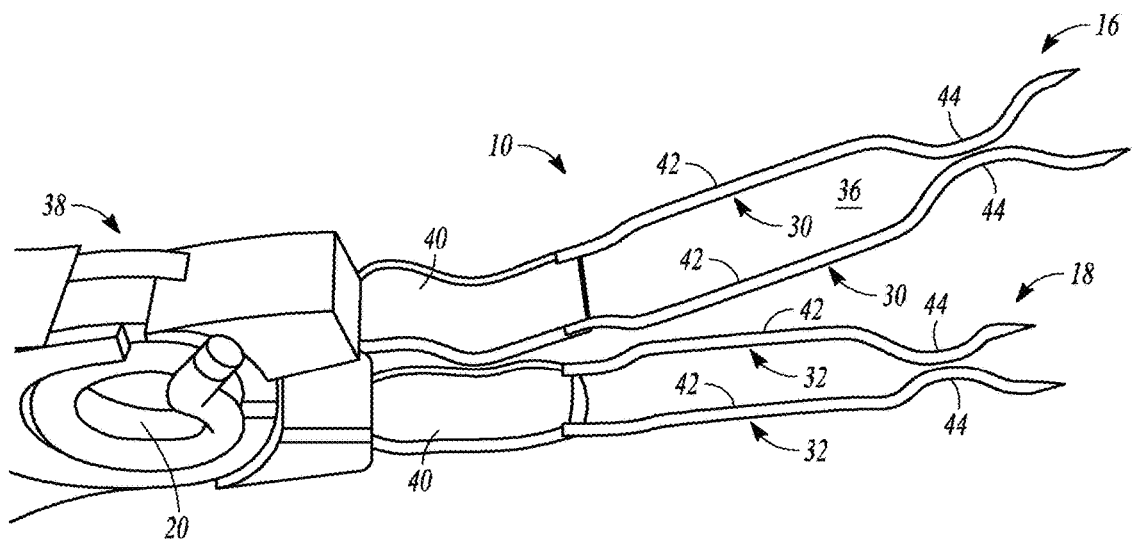
FIGS. 6A-6B show aspects of an anastomosis clip, according to example embodiments.
Figure 6B:
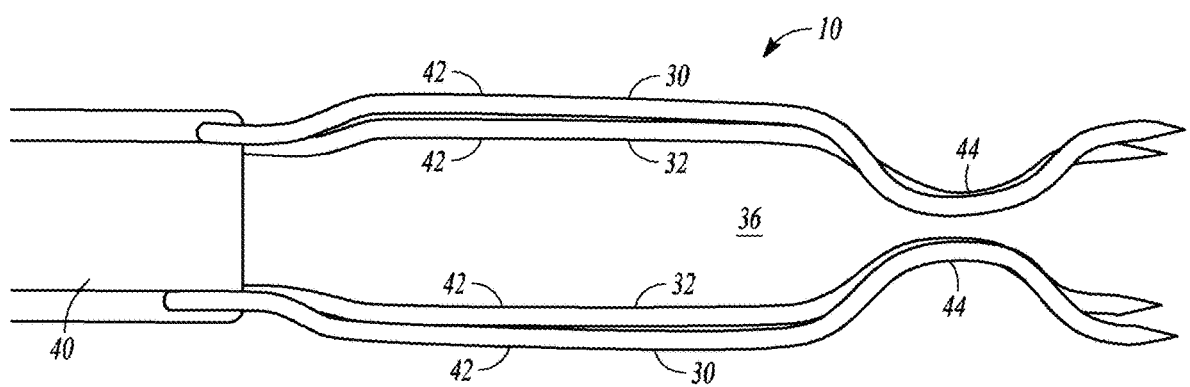

FIGS. 6A-6B generally depict an example anastomosis clip 10. The clip can include two sides 16 and 18 coupled together by means of an applicator shown generally at 38. In an example, the two sides 16 and 18 can be held and manipulated using opposed jaws 40 of the applicator 38. The sides 16 and 18 can move about a pivot axis 20 defined by the applicator 38. In some examples, the sides of the clip 10 are biased to a closed position by the applicator 38. In some examples, the jaws 40 are detachable from the applicator 38 and, in some examples, the sides 16 and 18 are detachable from the jaws 40. In some examples, the clip 10 or applicator 38 can include one or more biasing mechanisms of features of the type described above.

One or both sides 16 and 18 include attachment features configured to attach the side to a corresponding vessel. In the examples illustrated in FIGS. 6A-6B, attachment features are provided on both sides and include forks 30 and 32 configured to pierce the vessel wall. The forks 30 and 32 are two-pronged and assume a "bull-horn" configuration as shown. An example function of the bull horn is to match the puncture holes to the size of maximum lateral size of the metal ring in order to avoid extra stretch of the vessel wall, which potentially can reduce the chance of vessel damage during device positioning. Other configurations are possible. In some examples, the bull-horn forks are configured to assume a "side-by side" (FIG. 6B) configuration, or in some examples a "ring-on-ring" configuration, when the clip 10 is closed.

It will be appreciated that the substantially parallel, rectilinear portions 42 of the bull-horn forks 30 and 32 do not stretch the walls of the vessel as much as the rounder ring-shaped forks of the example clip 10 discussed further above, when inserted into the walls of a vessel. The narrower or straighter fork configuration can allow easier entry of the forks into the walls of a corresponding vessel.

As shown in FIGS. 6A-6B, distal portions 44 of the opposed forks 30 and 32 are shaped inwardly to define a substantially enclosed region 36 lying within the forks 30 and 32. The region 36 can, in similar manner to that described above, be used to provide a supported area for joining the walls of abutting vessels in "side-to-side" manner, or the end of a vessel to the wall of another vessel in "end-to-side" manner. While each side of the clip 10 is shown with a two-prong fork, it is contemplated that the sides of the anastomosis clip 10 include differently configured attachment features.

In some examples, a clip 10 includes a fork-ring combination such that a first side of the clip 10 includes attachment features (such as the example forks 30 and 32 of FIGS. 4A-6B), while a second side of the clip 10 includes a ring formation so that vessels can be joined in "side-to-end" manner. The second side of the clip may include a "closed ring" of the type shown in FIGS. 1A-3C, or in some examples may include an "open ring" forked configuration of the type shown in FIGS. 4A-6B (or any of the other examples described further below). In some examples, the second or "ring" side of the clip is used to secure a folded-over portion of an end of a vessel against the walls of another vessel which has been pierced and secured by the first or "forked" side of the clip. When closed, the clip 10 holds the two vessels together. A laser catheter or other device can be used to form a hole in the wall of the second vessel to allow passage of blood from the open end of the one vessel through the wall of the other vessel. As desired or appropriate, either side of the clip 10 can include attachment features or rings of any of the example embodiments described herein.

Figure 7A:
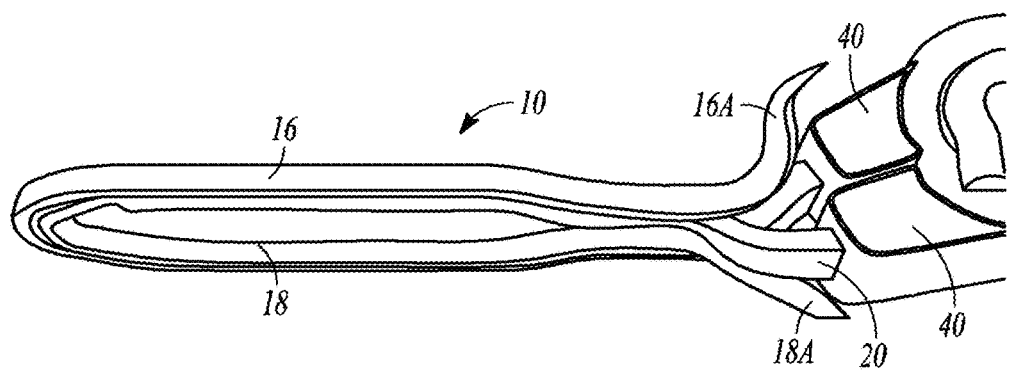
FIGS. 7A-7C show aspects of an anastomosis clip, according to example embodiments.
Figure 7B:
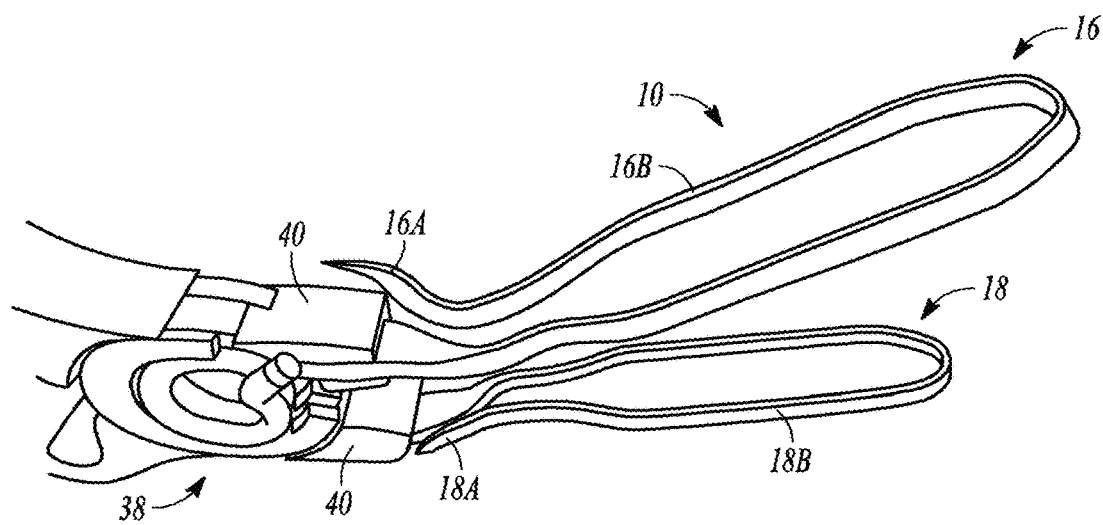
Figure 7C:
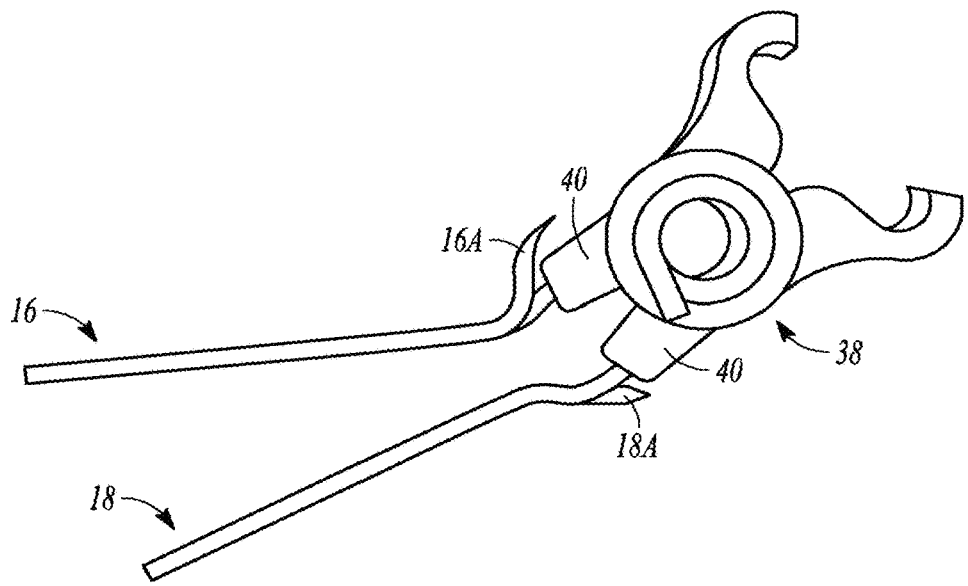
Figure 8A:
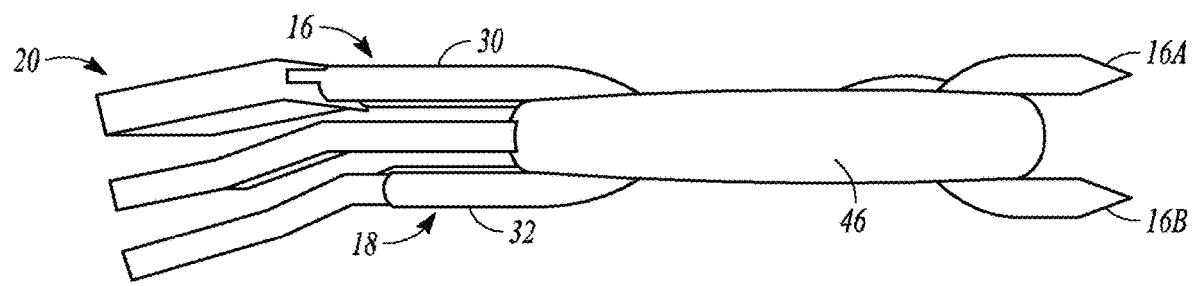
FIGS. 8A-8H show aspects of an anastomosis clip, according to example embodiments.
Figure 8B:
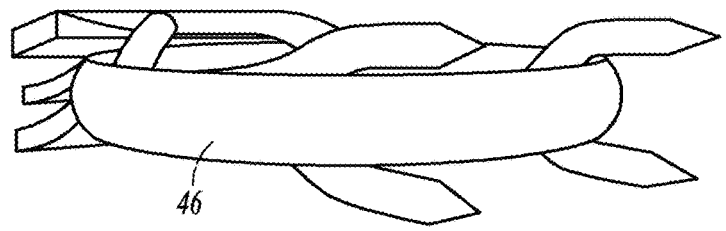
Figure 8C:
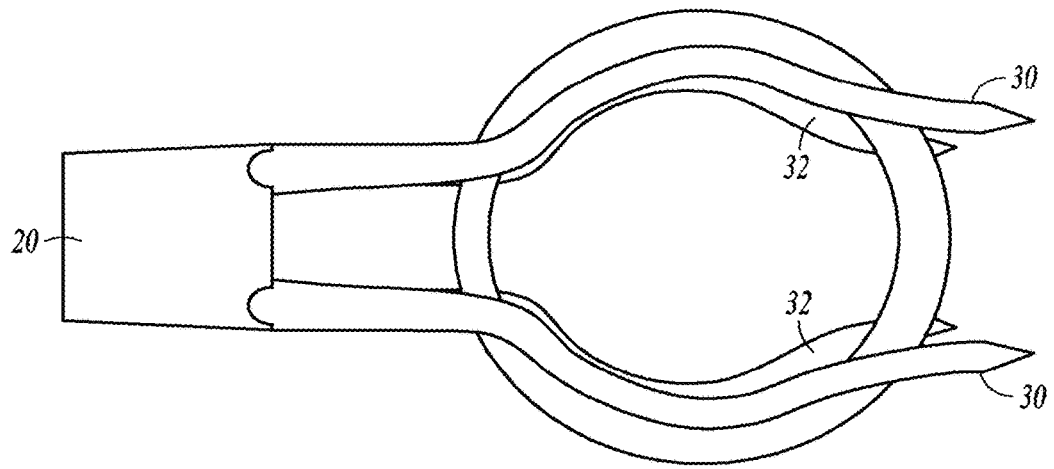
Figure 8D:
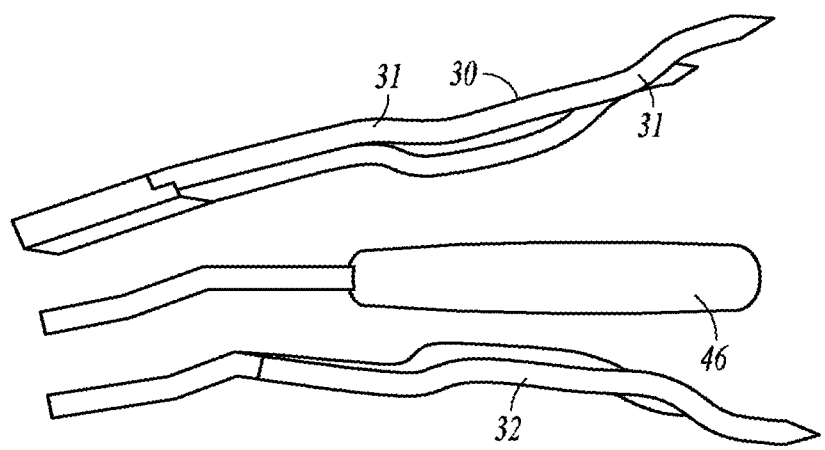
Figure 8E:
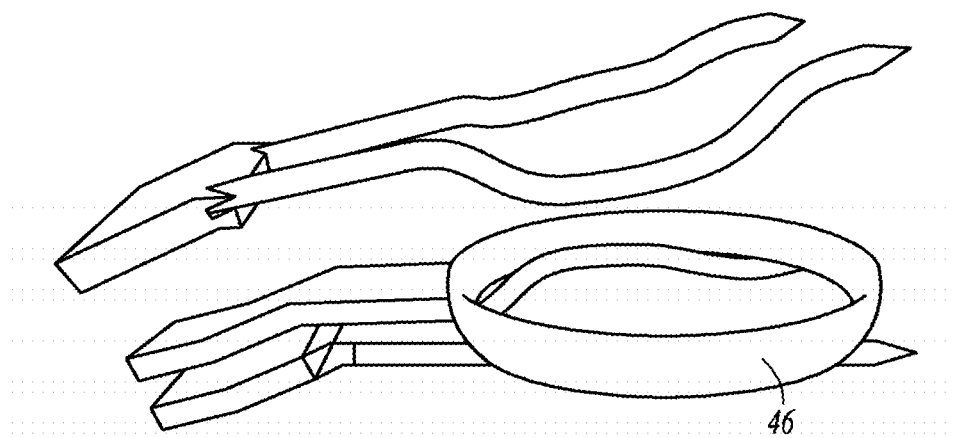
Figure 8F:
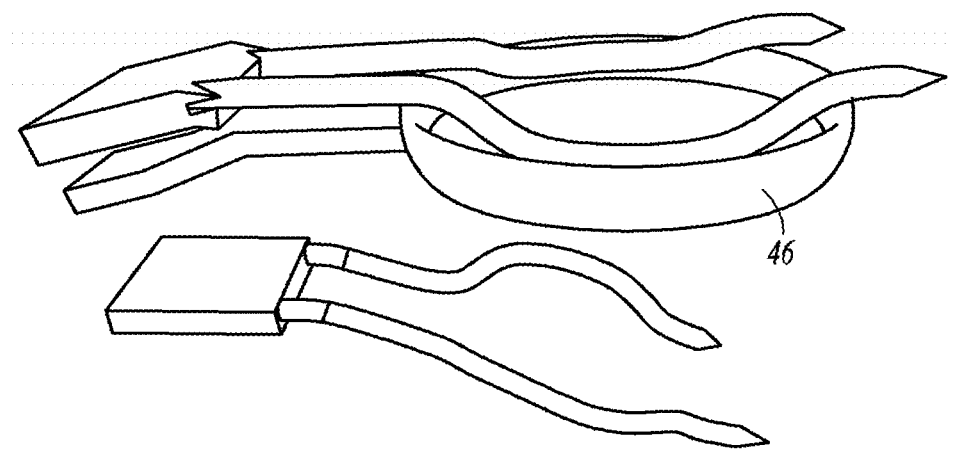
Figure 8G:
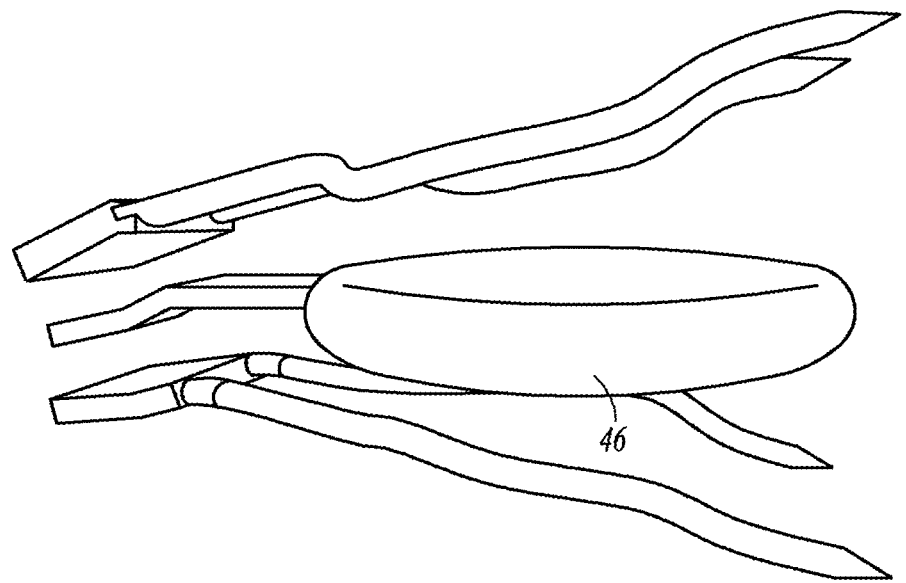
Figure 8H:
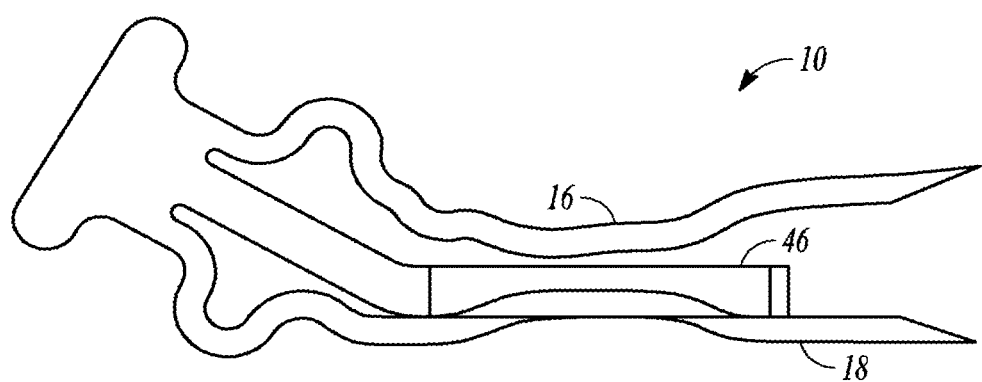

FIGS. 7A-7C generally depict an example anastomosis clip 10. The illustrated example clip 10 is of a general "paper-clip" configuration and includes two legs or loops that define (when the clip 10 is open) sides 16 and 18 of the clip 10 (FIG. 7C). In some examples, the legs of the sides 16 and 18 assume a nesting "side-by-side" configuration when the clip 10 is closed (FIG. 7A), while in some examples, the legs of the sides 16 and 18 lie one on top of another in a "ring-on-ring" configuration when the clip 10 is closed. Various combinations are possible. Each side of the clip 10 has only one vessel penetration pin or tip, in one example. In some examples, the other aspects of the clip operate in similar manner to other examples described in this specification.

In some examples, the sides 16 and 18 of the clip are joined together by a central hinge portion 20 formed integrally with the material of the clip 10, similar again to the structure of a paper-clip. In some examples, the sides 16 and 18 of the clip can be urged apart manually. In some examples, the sides 16 and 18 can be urged apart by an operator using the jaws 40 of an applicator 48 which engage with areas of the hinge portion 20 (FIGS. 7B-7C). In some examples, as the clip 10 is opened, the hinge portion 20 is deformed and the restorative force generated by the deformed material biases the sides 16 and 18 back into a closed position of the clip 10 (FIG. 7A). Other biasing mechanisms or features are possible, such as those described further above. In some examples, the deformed hinge portion 20 does not bias the clip but is sufficient to hold the clip in a desired position. In some examples, the hinge portion 20 is formed separately from the clip 10.

In some examples, a leg of each side 16 and 18 of the clip terminates at a proximal end in a curved, sharp portion indicated respectively by numerals 16A and 18A in FIGS. 7A-7C. The distal ends (i.e. away from the applicator) of each side 16 and 18 of the clip form hoops, similar again to a paper-clip. In some examples, the sharp portions 16A and 18A are carried by respective straight pin portions of the legs marked 16B and 18B in FIG. 7B. When the sides 16 and 18 of the clip 10 are moved apart (FIGS. 7B-7C), the sharp legs can more easily be inserted into the walls of respective donor and recipient vessels, for example. The sides 16 and 18 of the clip 10 can then be moved or released to hold the walls of the joined vessels together. In some examples, the entry of a single leg alone into each vessel results in only one point of entry in each vessel being formed accordingly. Reduction of entry points can be less traumatic to the vessel wall and can provide an advantage for the operator in being able to focus on one entry point only when inserting the clip. In some examples, the legs of the sides 16 and 18 assume round, oval, rectilinear, or other shapes or configurations in outline or cross-section. The legs may be of different sizes with respect to one another.

FIGS. 8A-8H generally depict an example anastomosis clip 10. This example clip is sometimes referred to as a "trinity" clip in that it can comprise three parts: two sides 16 and 18, and a retainer member 46. In some examples, the clip nevertheless operates in similar manner to other examples described in this specification, and can provide the same advantages. The shape of the sides and/or forks of the clip can be as shown in the example drawings in FIGS. 8A-8H or can have the bull horn configuration or paper clip configuration or a combination of the configurations for each side, ring, or fork. In some examples, a retainer member 46 is interposed, or at least interposable, between the sides 16 and 18 of the clip 10. The retainer member 46 can allow a donor vessel connection and a recipient vessel connection to be opened or closed independently of each other. One side 16 of an installed clip 10 acting, for instance, against the retainer member 46 to close a donor vessel connection (with or without closing bias), can be left intact (i.e. in closed position) while the other side 18 of the clip can be opened or moved away from the retainer member 46 to open, for instance, a recipient vessel connection. The thus-opened recipient connection can be closed again, as desired, without disturbing the donor connection on the other side of the clip 10. The independent opening and closing of connections can allow improved fixation and stability of a surgical site while allowing more control of blood flow, the introduction of catheters, and so forth.

Turning again to FIGS. 8A-8H, an example anastomosis clip 10 includes two sides 16 and 18 coupled together. In some examples, the two sides are hinged together shown generally at 20. In some examples, the hinge 20 of the clip 10 is biased to a closed position. In some examples, the clip 10 includes formations or mechanisms so that one or more of the sides 16 and 18 can be manipulated, with or without associated movement of the retainer member 46. In some examples, the sides 16 and 18 of the clip 10 can be manipulated with an applicator. In some examples, the clip 10 can include one or more biasing mechanisms or features, including for example the biasing mechanisms of features described further above.

In some examples, each of the sides 16 and 18 includes attachment features configured to attach each of the sides to a corresponding vessel. In some examples, the attachment features include forks 30 and 32 configured to pierce the vessel wall. While each side is shown with a two-prong (or paired) fork, it is contemplated that the sides of the anastomosis clip 10 include differently configured attachment features. In some embodiments, the ends of the forks 30 and 32 are sharp to pierce the vessel wall. In some examples, the retainer member 46 is fixed to the clip, or may be attached to or form part of the hinge 20. In some examples, the retainer member 46 is free and unattached to the clip. A clip kit including a clip 10 (as described in any of the examples above) and a separate retainer member 46 (configured to be interposable between the sides) may be provided. In some examples, the retainer member includes a ring structure, including for example a structure substantially as shown in FIGS. 8A-8H. Other configurations, structures and shapes of retainer member 46 are possible. The configurations, structures and shapes of the retainer member may be selected to cooperate with the attachment features of the clip, or the size of the vessels to be joined, for example. In some examples, an attachment feature of one or both sides 16 and 18 of the clip 10 is shaped or bent (for example, at 31 in FIG. 8H) so that at least a portion of the attachment feature lies within the retainer member 46 when the clip 10 is closed. The sides 16 and 18 of the clip 10 may, in conjunction with the retainer member 46 or independently thereof, form "side-by-side" or "ring-on-ring" configurations of the type described above when brought together. Each or both of the sides 16 and 18 of the clip 10 may include one or more of the example rings and attachment features described herein, or variants thereof. In some examples, a second or more retainer members 46 are provided. For example, a clip 10 may include two ring structures 46 interposed between the sides 16 and 18 of the clip 10, and hence comprise four parts.

As with the examples described above, installation of the clip 10 can proceed as follows. The clip 10 is opened (or otherwise manipulated when closed, depending on the overall configuration of the clip 10, or its respective sides 16 and 18 and attachment features, and so forth) so that one side 16 of the clip 10 is inserted into the wall of a first vessel (such as a donor vessel), and the other side 18 of the clip is inserted into the wall of a second vessel (such as a recipient vessel). The clip 10 can be used as appropriate to form end-to-end, side-to-side, or end-to-side vessel connections. In a side-to-side vessel connection, for example, the retainer member 46 lies in use between the outer surfaces of the walls of the adjoining vessels and defines a reaction surface against which the sides 16 and 18 of the clip 10 (inserted within the corresponding vessel wall) can push or engage the vessel walls to close a corresponding vessel connection. This arrangement is shown for example in schematic sectional outline in FIG. 8H. The vessel walls have been omitted in this view in the interest of clarity, but it will be appreciated that the "upper" side 16 of the clip can be moved (as desired) towards or away from the retainer member 46 and independently of the "lower" side 18 of the clip 10, which can do the same. Once the clip 10 has been installed in the vessel walls, a hole can be formed (by a laser catheter or other device, for example) to pass though through the walls of the adjoining vessel walls and through the center of the retainer member 46. In some examples, the pins or forks on a side 16 or 18 of the clip 10 are first advanced into a donor vessel. The clip 10 is closed and the donor vessel wall is captured between the retainer member (e.g. ring 46) of the clip and the pins in the donor vessel wall. A hole can be formed or burned by advancing a laser catheter (or other device, for example) via the distal end of the donor vessel. Then the other side of the clip (18 or 16, respectively—lower part of the clip 10 in the view) can be opened while donor vessel (which has already been holed) is held in place by the retainer member 46. Now the pins or forks on the other side of the clip 10 can be introduced into a recipient vessel and clip 10 can be closed. Now the catheter (or other device) can be positioned again and will form or burn a hole in the recipient vessel. Again the retainer member 46 will give stability to the recipient vessel and the introduced pins or forks. The shape of the clip sides 16 and 18, the pins or forks, and the retainer member 46, can be configured in such a way that the vessel walls are pushed on top of each other so that good connection is facilitated.

Figure 9A:
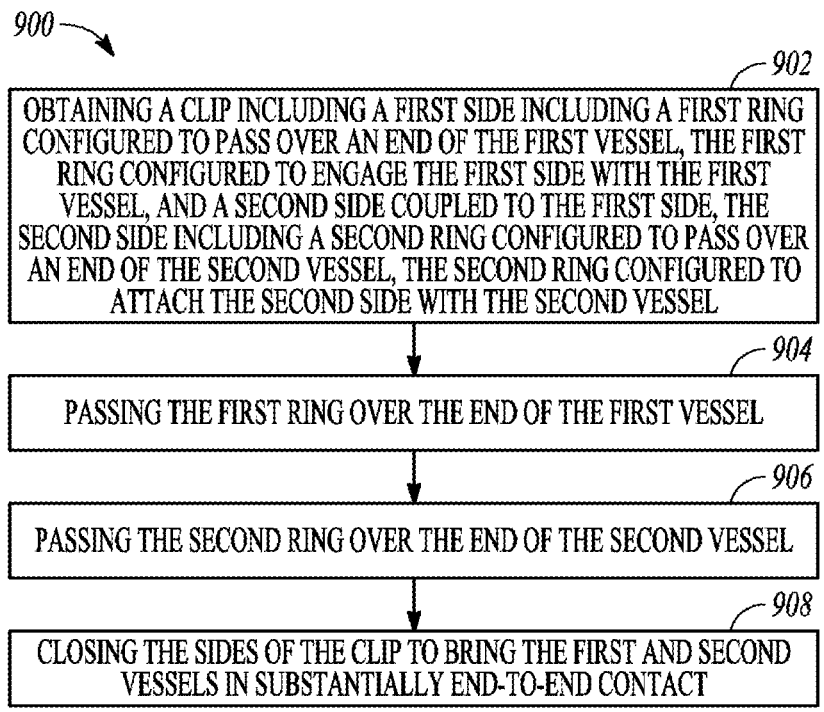
FIGS. 9A-9B are block flow diagrams depicting aspects of methods for facilitating connection of first and second vessels, according to example method embodiments.

Some embodiments of the present inventive subject matter include methods for facilitating connection of first and second vessels. One such embodiment is illustrated in FIG. 9A. In some embodiments, a method 900 includes: at element 902, obtaining a clip including a first side including a first ring configured to pass over an end of the first vessel, the first ring configured to engage the first side with the first vessel, and a second side coupled to the first side, the second side including a second ring configured to pass over an end of the second vessel, the second ring configured to attach the second side with the second vessel; at element 904, passing the first ring over the end of the first vessel; at element 906, passing the second ring over the end of the second vessel; and, at element 908, closing the sides of the clip to bring the first and second vessels in substantially end-to-end contact.

In some examples, the method 900 further comprises folding a portion of the end of the first or second vessel over the first or second ring; and attaching the first or second ring to the folded-over portion of the first or second end, respectively. The first or second side of the clip may include respective first or second attachment features, the first or second attachment features including points configured to puncture a wall of the first or second vessel.

In some examples, the wall is a wall of the first or second folded-over portion, and the method 900 further comprises inserting the points into the wall to attach the first or second ring to the folded-over portion of the first or second vessel end, respectively.

The first and second sides of the obtained clip may be biased to a closed position, and the method 900 may further comprise closing the sides of the clip to maintain the first and second vessels in substantially end-to-end contact.

Figure 9B:
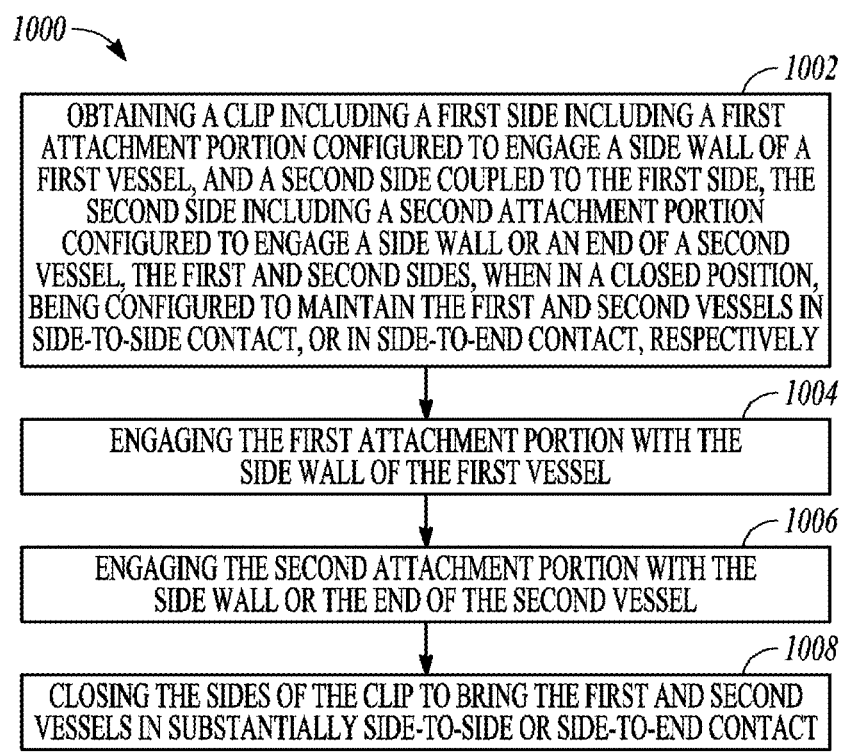

With reference to FIG. 9B, a method 1000 includes: at element 1002, obtaining a clip including a first side including a first attachment portion configured to engage a side wall of a first vessel, and a second side coupled to the first side, the second side including a second attachment portion configured to engage a side wall or an end of a second vessel, the first and second sides, when in a closed position, being configured to maintain the first and second vessels in side-to-side contact, or in side-to-end contact, respectively; at element 1004, engaging the first attachment portion with the side wall of the first vessel; at element 1006, engaging the second attachment portion with the side wall or the end of the second vessel; and, at element 1008, closing the sides of the clip to bring the first and second vessels in substantially side-to-side or side-to-end contact.

In some examples, the first and second sides of the obtained clip are biased to a closed position, and wherein closing the sides of the clip includes maintaining the first and second vessels in substantially side-to-side or side-to-end contact.

The first or second attachment portion may include points or at least one fork configured to puncture the side wall or end of the respective first or second vessel, and wherein the method further includes inserting the points or the at least one fork into the side wall or end of the first or second vessel thereby to engage the first or second side of the clip with the respective side wall or end of the first or second vessel.

In some examples, the first or second attachment portion includes a pair of forks for piercing the side wall of the first or second vessel, the pair of forks defining an outline that can stretch or support a portion of the side wall disposed between the forks when the forks are embedded in the side wall of the first or second vessel. The method 1000 may further comprise inserting the pair of forks into the side wall of the respective first or second vessel, and supporting or stretching a portion of the side wall disposed between the inserted forks.

In some examples, the obtained clip includes a retainer member interposable between the first and second side soft the clip, the retainer member being configured to engage with a side of the clip to open or close a connection between the first and second vessels, the method further comprising opening or closing at least one of the sides of the clip to open or close the connection. The method 1000 may further comprise forming a hole in the side wall of the first or second vessel.

ADDITIONAL NOTES

The patent or application file, including the file of related applications, may contain at least one drawing executed in color. Copies of this patent or patent application publication with color drawing(s) will be provided by the Office upon request and payment of the necessary fee.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:
1. An anastomosis clip for connecting a first vessel with a second vessel,
  wherein the first and second vessels each have a vessel wall with an outer surface,
  wherein the anastomosis clip comprises:
    a first attachment portion,
    a second attachment portion,
    a hinge having a pivot axis and configured to couple the first attachment portion to the second attachment portion such that the first attachment portion and the second attachment portion are movable relative to one another around the pivot axis between i) a closed position and ii) an open position, and
    a retainer ring which is moveable relative to the first attachment portion as well as to the second attachment portion and which is configured to lie, in use, between the outer surfaces of the vessel walls of the first and second vessels;
  wherein, in the closed position, the first attachment portion and the second attachment portion are arranged substantially parallel to each other with the retainer ring being interposed between the first and second attachment portions;
  wherein, in the open position, the first attachment portion and the second attachment portion are arranged at a non-zero angle with respect to each other; and
  wherein, the first attachment portion, the second attachment portion, and the retainer ring are configured in such a way that, when in the closed position:

i) a part of the first attachment portion extends parallel to a part of the retainer ring to engage, in use, the wall of the first vessel between said part of the first attachment portion and a first reaction surface of said part of the retainer ring,
ii) a part of the second attachment portion extends parallel to said part of the retainer ring to engage, in use, the wall of the second vessel between said part of the second attachment portion and a second reaction surface of said part of the retainer ring, and
iii) the first attachment portion is movable away from the retainer ring while the second attachment portion remains parallel to the retainer ring and/or the second attachment portion is movable away from the retainer ring while the first attachment portion remains parallel to the retainer ring;

wherein the first reaction surface and the second reaction surface face in mutually opposite directions, wherein the part of the first attachment portion, which in the closed position extends parallel to said part of the retainer ring, lies within the retainer ring when in the closed position, and wherein the part of the second attachment portion, which in the closed position extends parallel to said part of the retainer ring, lies within the retainer ring when in the closed position.

* * * * *